US00PP25693P2

(12) United States Plant Patent
Boos

(10) Patent No.: US PP25,693 P2
(45) Date of Patent: Jul. 14, 2015

(54) **VARIETY OF *PRUNUS* ROOTSTOCK NAMED 'A B 207'**

(50) Latin Name: *Prunus*
Varietal Denomination: A B 207

(71) Applicant: Albert Boos, Reedley, CA (US)

(72) Inventor: Albert Boos, Reedley, CA (US)

( * ) Notice: Subject to any disclaimer, the term of this patent is extended or adjusted under 35 U.S.C. 154(b) by 0 days.

(21) Appl. No.: 14/121,160

(22) Filed: Aug. 6, 2014

(51) Int. Cl.
*A01H 5/08* (2006.01)

(52) U.S. Cl.
USPC ..... Plt./183

(58) Field of Classification Search
USPC ..... Plt./183, 184
CPC ..... A01H 5/0862
See application file for complete search history.

(56) References Cited

U.S. PATENT DOCUMENTS

| | | | |
|---|---|---|---|
| PP8,037 | P | 11/1992 | Wuhl |
| PP10,385 | P | 5/1998 | Zaiger et al. |
| PP11,403 | P | 6/2000 | Doyle et al. |
| PP12,856 | P2 | 8/2002 | Zaiger et al. |
| PP21,248 | P2 | 8/2010 | Slaughter et al. |
| PP21,533 | P3 | 11/2010 | Pinochet |
| PP23,583 | P2 | 5/2013 | Beckman et al. |
| PP23,631 | P2 | 5/2013 | Bliss et al. |

*Primary Examiner* — Keith O. Robinson
(74) *Attorney, Agent, or Firm* — Mark D. Miller

(57) ABSTRACT

Disclosed is a new and distinct variety of prunus rootstock useful for peach, plum, nectarine, apricot, cherry and potentially other scionic and stone fruit varieties; and particularly useful for plum varieties such as 'Crimson Glow' and/or 'Black Splendor' and/or 'Jo Anna Reds'. The present variety appears has considerable tolerance to infection by *Armillaria* (aka Oak Root Rot) which is a common root fungi, infecting many soils in California, particularly where oak trees have been grown.

7 Drawing Sheets

Latin name: *Prunus*.
Varietal denomination: 'A B 207'.

BACKGROUND OF THE NEW VARIETY

The present invention relates to a new and distinct variety of *Prunus* rootstock which will hereinafter be denominated varietally as the 'A B 207 Rootstock'. This rootstock is particularly tolerant to the *Armillaria* fungus, commonly known as causing a destructive root and crown rot of the tree.

The *Armillaria* fungus is commonly referred to as the Oak Root Rot or Honey Fungus. The fungus is a potent parasite on many fruit tree crops including stone fruit. The usual species associated with this malady is *A. mellea*. This fungus has global distribution in stone fruit cultivation and is prevalent in the Central Valley of California, where oak trees are common. When such oak trees are removed or die, the fungus tends to remain in the ground. Subsequent plantings of virtually any tree or vine in the vicinity where the oak tree had been planted, usually result in some degree of infection of the planted tree crop. The disease is typified by non-random spread along tree rows due to root anastomosis between adjacent trees, providing an ideal infection route for this root infecting fungal pathogen. Most plants are eventually overcome by the fungus. Mature trees usually succumb over several years, generally leading to entire orchard death. The fungus can survive in the soil for long periods of time (years), and currently no prophylactic chemical control is available. Generally fumigation is utilized prior to new plantings to eradicate the fungus. However, due to the wide host range of this fungus, the fungus is rarely eliminated but usually only partially controlled.

Long term durable control of soil-borne diseases is most effectively achieved through plant tolerance selection. However, in the case of resisting *Armillaria* in stone fruit, numerous different rootstocks have been tried in diverse geography including California with little success. This new discovery represents a significant improvement in the development of a rootstock tolerant to this serious pathogen. In addition, the rootstock of the present invention is useful for varieties such as 'Crimson Glo' (U.S. Plant Pat. No. 12,856) and 'Black Splendor' (unpatented) and 'Joanna Red' (U.S. Plant Pat. No. 10,385) and the rootstock of the present invention appears to also be available for use with peach and nectarine (*Prunus persica*) scions.

Origin and Asexual Reproduction of the New Variety

The new variety was discovered by the inventor in a cultivated field of plum trees (*Prunus*) in Reedley, Calif. By way of background, the inventor planted approximately 30 plum trees in 1978 using a rootstock known as '2624'. The inventor noticed a difference in one of the trees from this rootstock, and planted a cutting from this tree (hereafter G1—the parent of the present invention) in an adjacent field in 1980. Numerous cuttings from the G1 tree were planted in 1983, and grafted over to 'Friar' (unpatented) and 'Showtime' (U.S. Plant Pat. No. 8,037) plums. During that same year (1983), the inventor purchased numerous additional trees of the 'Friar' (unpatented) and 'Showtime' (U.S. Plant Pat. No. 8,037) plum varieties which had been grafted on a 'Marianna' (unpatented) rootstock. The trees on the G1 rootstock and those on the 'Marianna' (unpatented) rootstock grew in adjacent fields for approximately 20 years.

It is significant that in approximately 2003, the inventor found it necessary to prune back the plum trees on the 'Marianna' (unpatented) rootstock in order to cause the fruit on these trees to be the same size as the fruit on the un-pruned trees with the G1 rootstock. Since 2003, the fruit size produced by the trees on both the 'Marianna' (unpatented) rootstock and the G1 rootstock has been approximately the same, but the annual fruit production (number of plums per tree) on the pruned 'Marianna' (unpatented) trees has been substantially lower (by over 75%) than the production of the G1 trees of the same age. Meanwhile, beginning in approximately 2000, many of the trees on the 'Marianna' (unpatented) rootstock began to die from the *Armillaria* (Oak Root) fungus.

In approximately 2007, a cutting from the G1 tree (which is the new and distinct variety (G2) referred to herein as the 'A B 207' rootstock) was planted in an area where some of the former 1983 'Marianna' (unpatented) trees had been, and which had succumbed to the *Armillaria* fungus. The 'A B 207' rootstock was allowed to grow and has shown resistance to the *Armillaria* fungus. Asexual reproduction of the new and distinct variety was carried out in Reedley, Calif. and accomplished by taking cuttings from the 2007 plant and planting the same in an adjacent location in Reedley, Calif., during the dormant season of 2012. 'Friar' (non-patented) plum scions were grafted onto these rootstocks in 2013. Additional cuttings from the 2007 plant were planted in 2013. Some of the 2013 plantings were left un-grafted.

Subsequent evaluations have shown the asexual reproduction to run true to the original tree. All characteristics of the original tree were established, and appear to be transmitted through succeeding asexual reproductions.

SUMMARY OF THE NEW VARIETY

The subject 'A B 207' rootstock is a new and distinct variety of rootstock which appears to be quite useful for peach, plum, nectarine, apricot, cherry and potentially other scionic and stone fruit varieties; and useful for plum varieties such as 'Crimson Glo' (U.S. Plant Pat. No. 12,856) and/or 'Black Splendor' (unpatented) and/or 'Joanna Red' (U.S. Plant Pat. No. 10,385). The present variety appears novel in view of its considerable tolerance to infection by *Armillaria* (aka Oak Root Rot) which is a common root fungi, infecting many soils in California, particularly where oak trees have been grown.

DETAILED DESCRIPTION

Referring more specifically to the horticultural details of the new and distinct variety of rootstock, the following details have been observed on one-year old plants during the second season (un-grafted 2013 plantings) under the ecological conditions prevailing at the orchard of origin which is located near Reedley, Calif. in the San Joaquin Valley of Central California.

The new variety exhibits similar good tolerance to calcareous soils and sandy soils, moderate root-knot nematode, and resistance to several soil-borne fungi, especially *Armillaria* mellea. The selection has medium chilling requirements. It differs from the known maternal parent in its leaf shape, vigor, and the fact that it better tolerates *Armillaria* root rot. In particular, the leaf petiole of the new 'A B 207 variety is devoid of vestigial wings found in the parent. The new 'A B 207' variety has better vigor than the parent. The new 'A B 207' variety tolerates *Armillaria* root rot longer than the parent. The new variety has been established in the field for the last several years and been found to retain its distinctive characteristics and remain true to type through successive propagations. The following characteristics distinguish this selection from other known varieties:

- Moderate vigor with a small trunk cross-section area;
- High capacity to control tree vigor when grafted with peach and nectarine varieties (recommended use);
- Tolerance to root asphyxia;
- Tolerance to alkaline soils.
- Moderate resistance to root-knot nematodes (*Meloidogyne* spp.);
- Tolerance to the lesion nematode *Pratylenchus vulnus;*
- Induces larger sized fruit in plum, peach and nectarine varieties and hence less need for thinning;
- Medium chilling requirements within the range of 600 to 800 cu.; and
- Resistance to *Armillaria* root rot.

DESCRIPTION OF THE DRAWINGS

The accompanying drawings are color photographs showing the tree, leaves and branches of the new variety with the color being as nearly true as is possible with color illustrations of this type.

Figure 1:
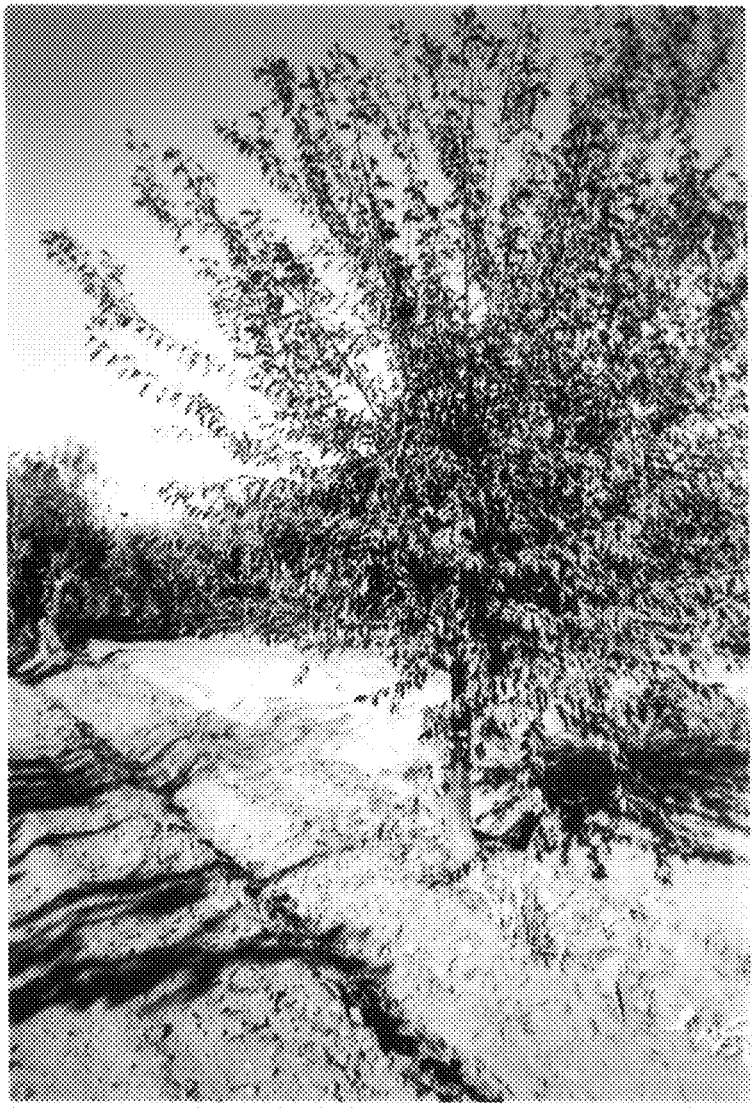
FIG. 1 shows an entire tree of the new variety, planted in 2007 (six year old tree).
Figure 2:
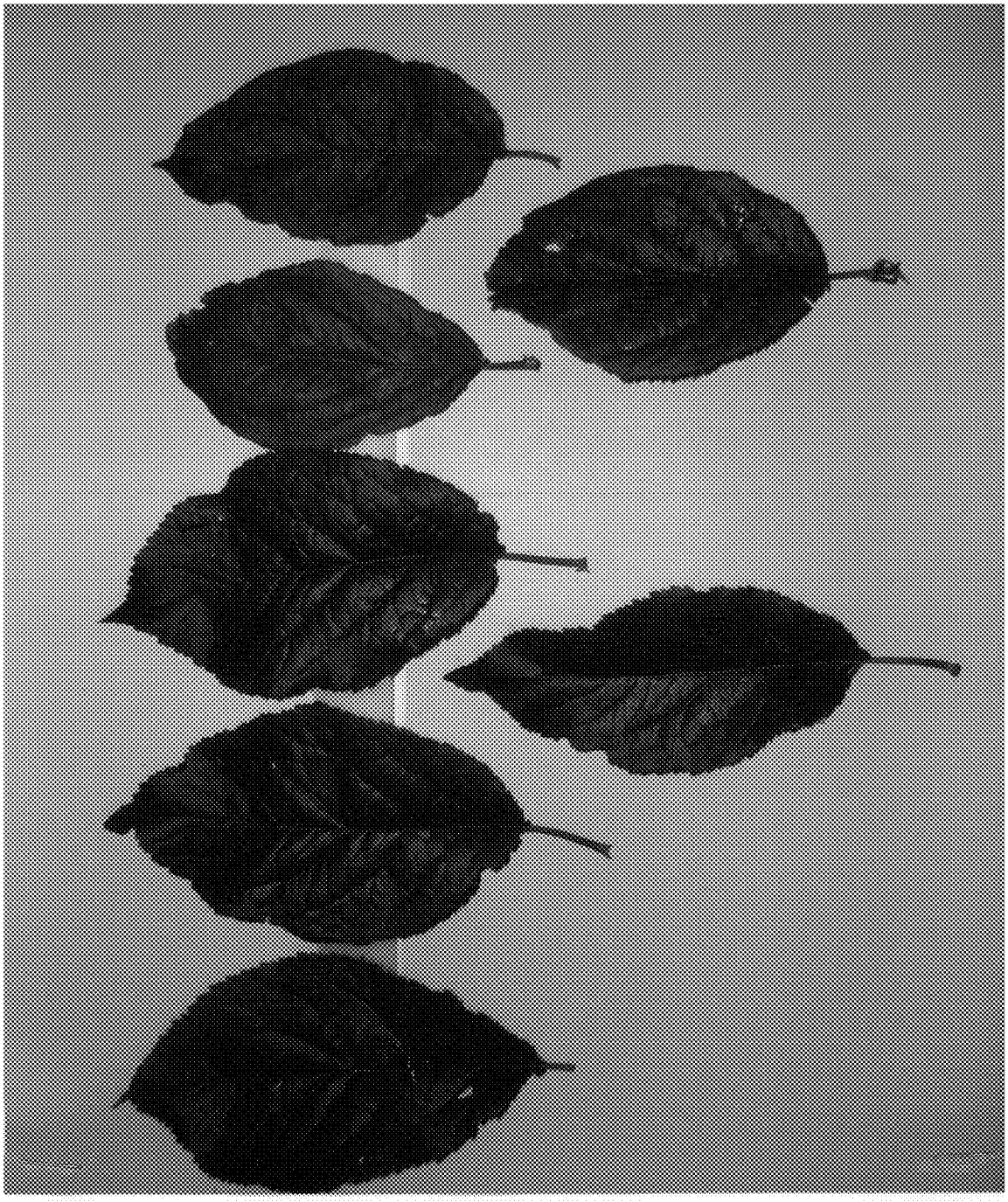
FIG. 2 shows the leaves of the new variety (one year old planting).
Figure 3:
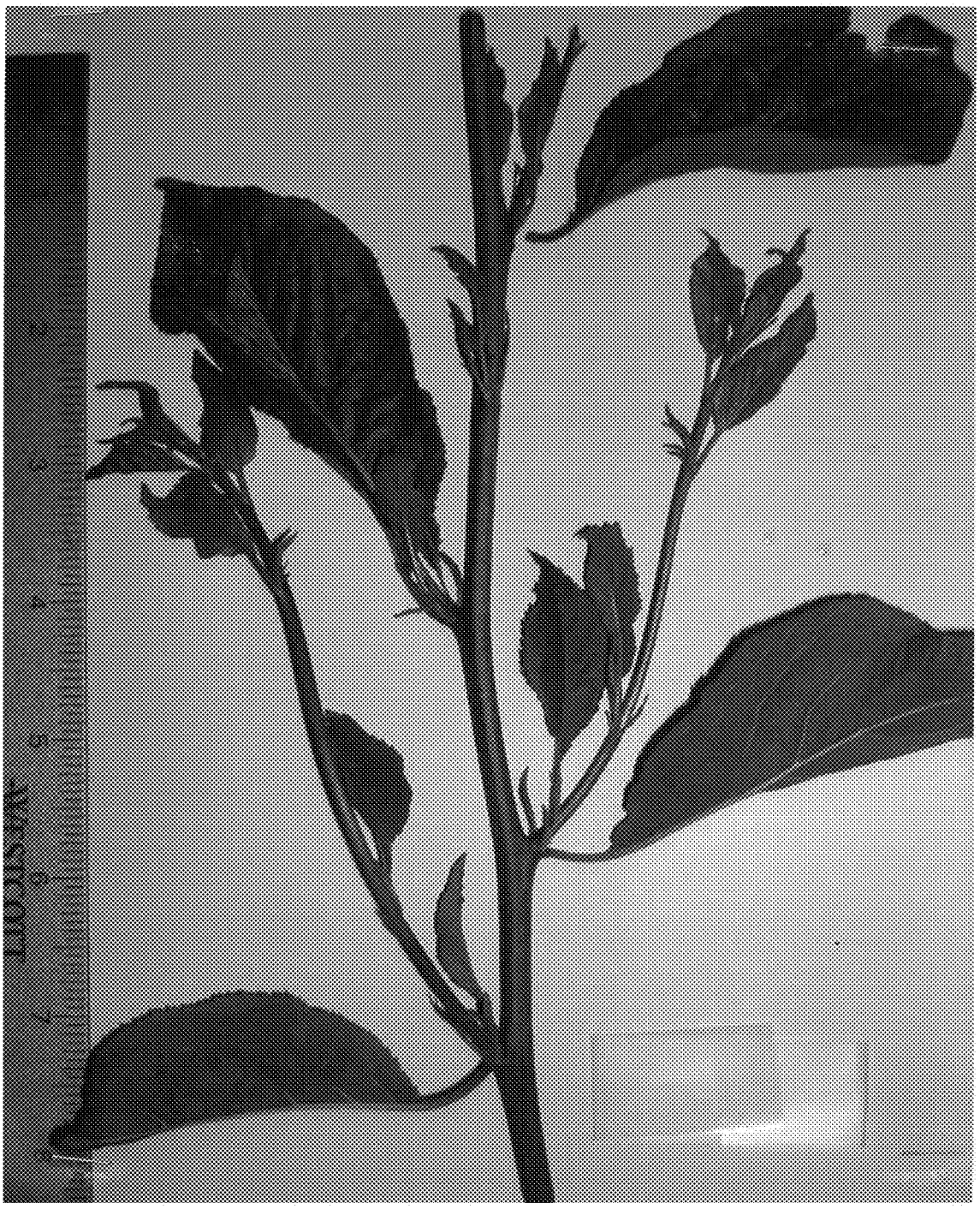
FIG. 3 shows stem leaf branch characteristics of the new variety (one year old planting).
Figure 4A:
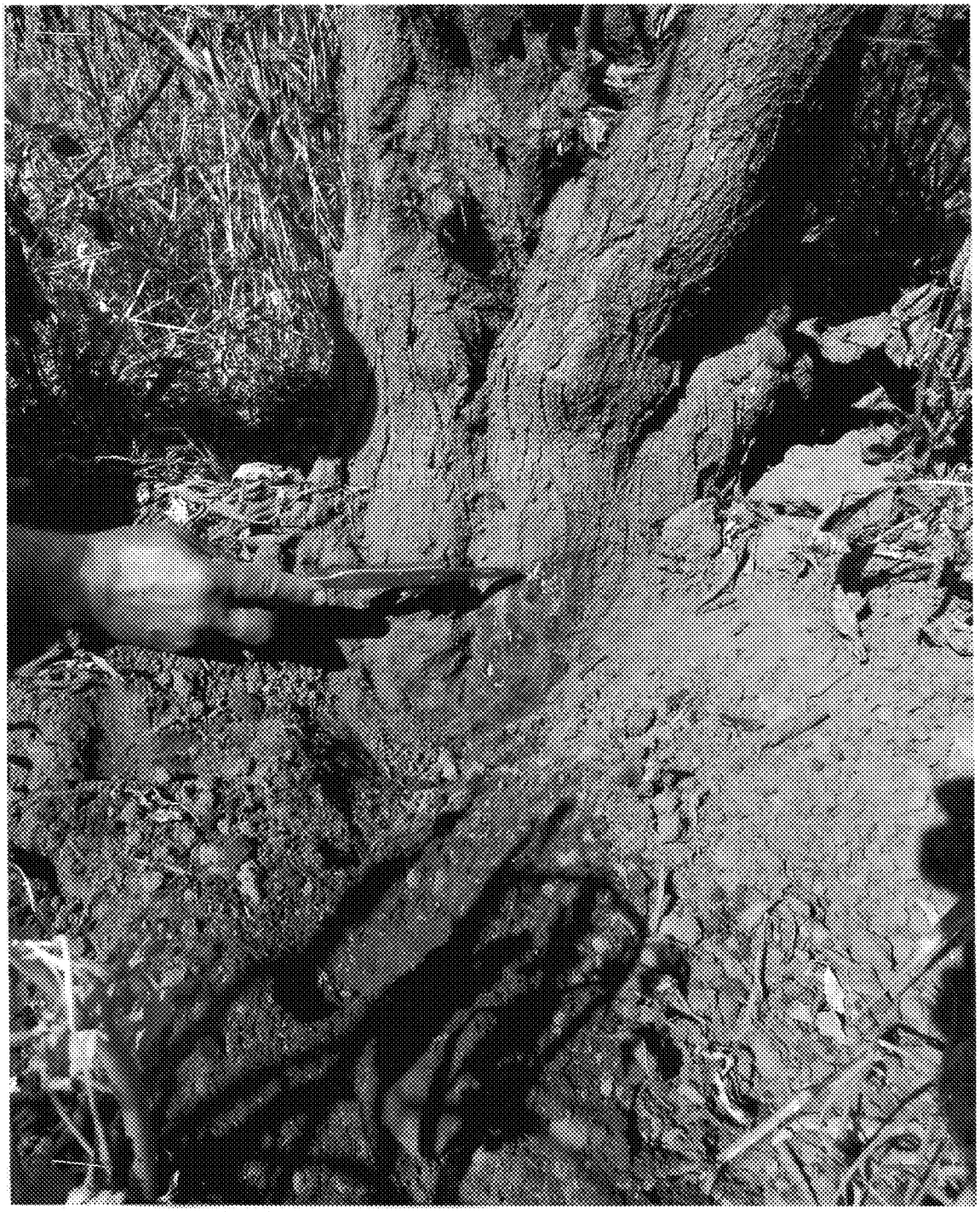
FIGS. 4A and 4B show evidence of *Armillaria* root rot on rootstock in the orchard where the present variety was planted.
Figure 4B:
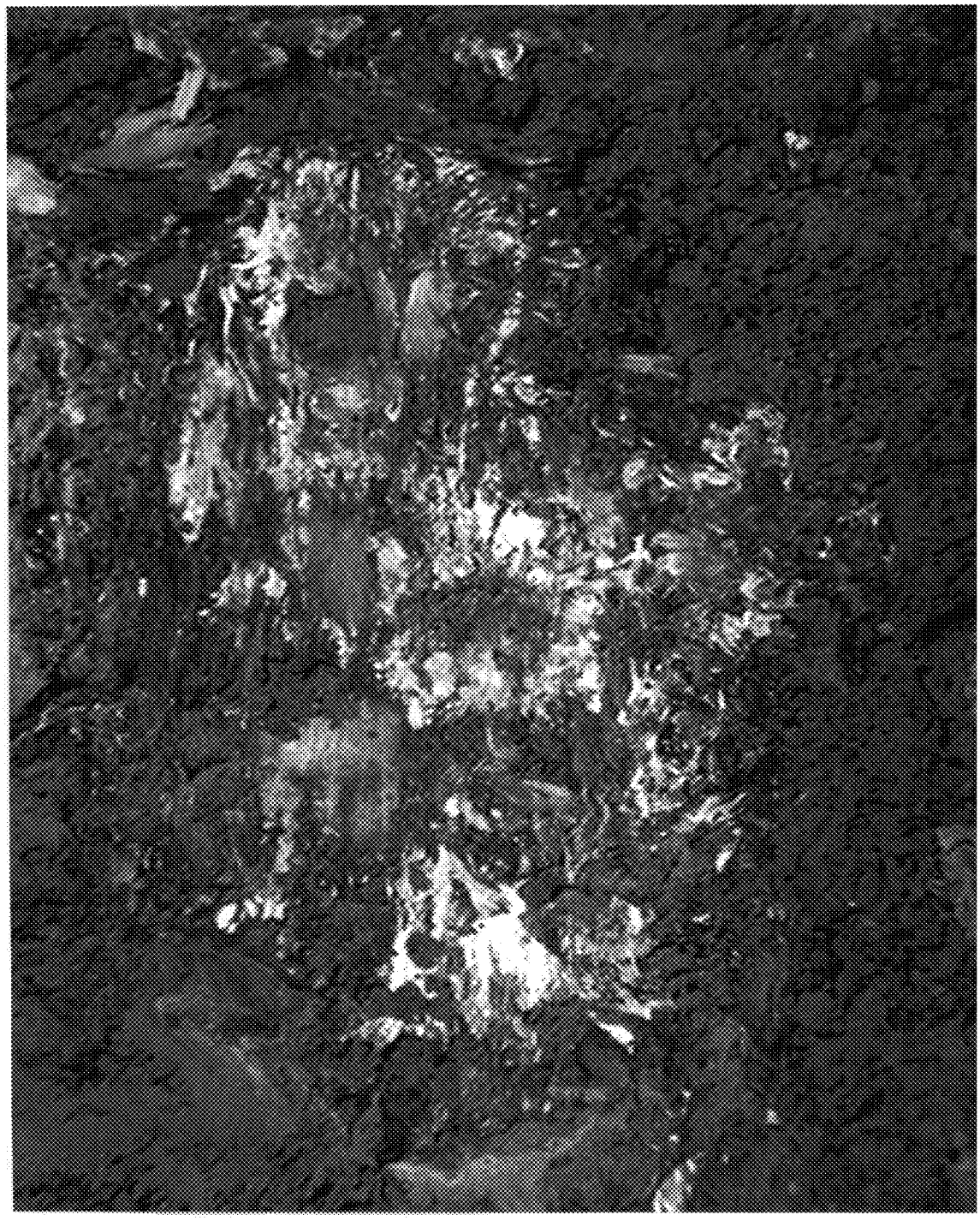
Figure 5A:
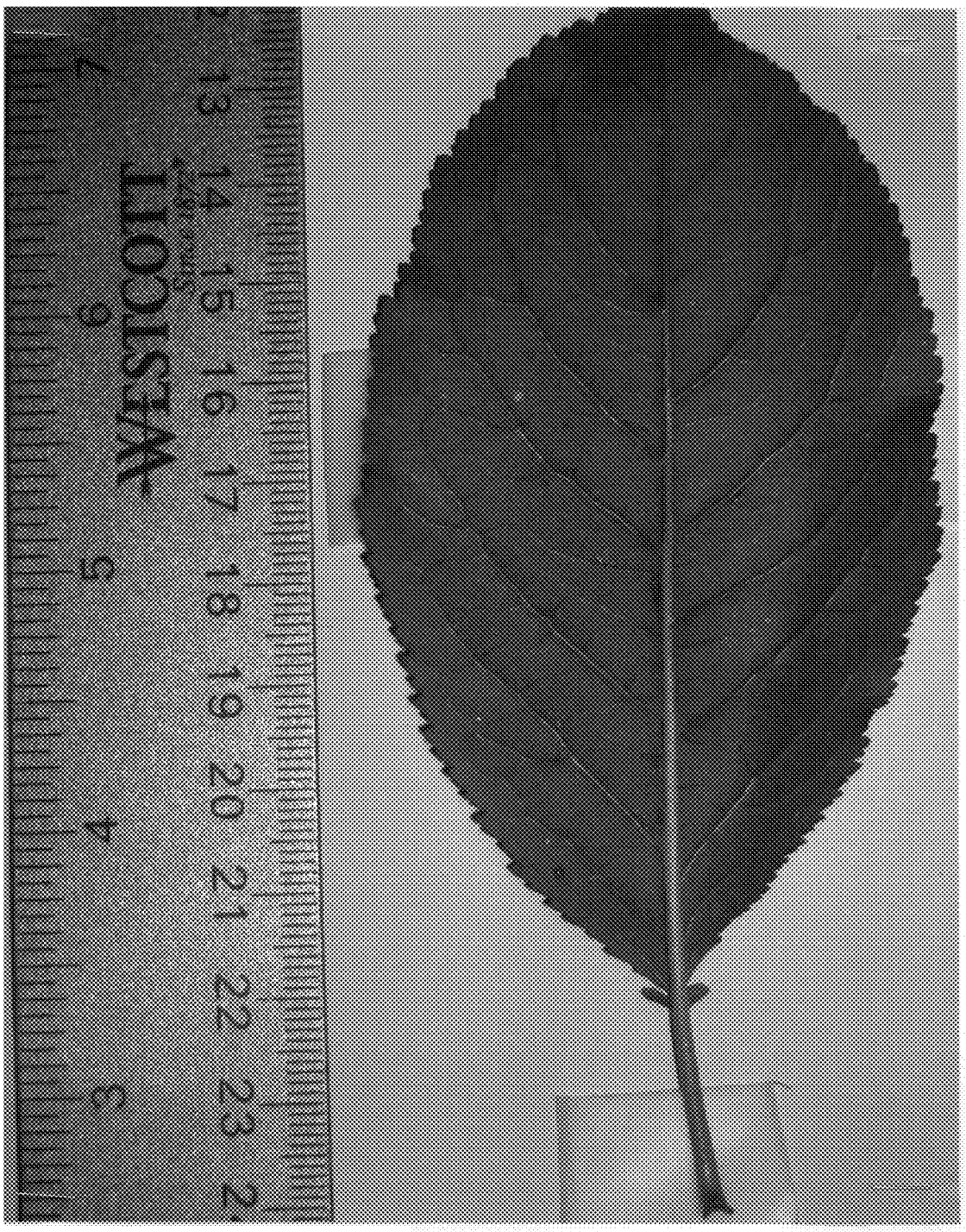
FIGS. 5A and 5B show a comparison of the leaf petiole differences between the parent G1 and the present variety G2 ('A B 207'). The present variety G2 ('A B 207') shown in FIG. 5B (one year old planting) has a distinct lack of vestigial wings as compared to the parent G1 shown in FIG. 5A.
Figure 5B:
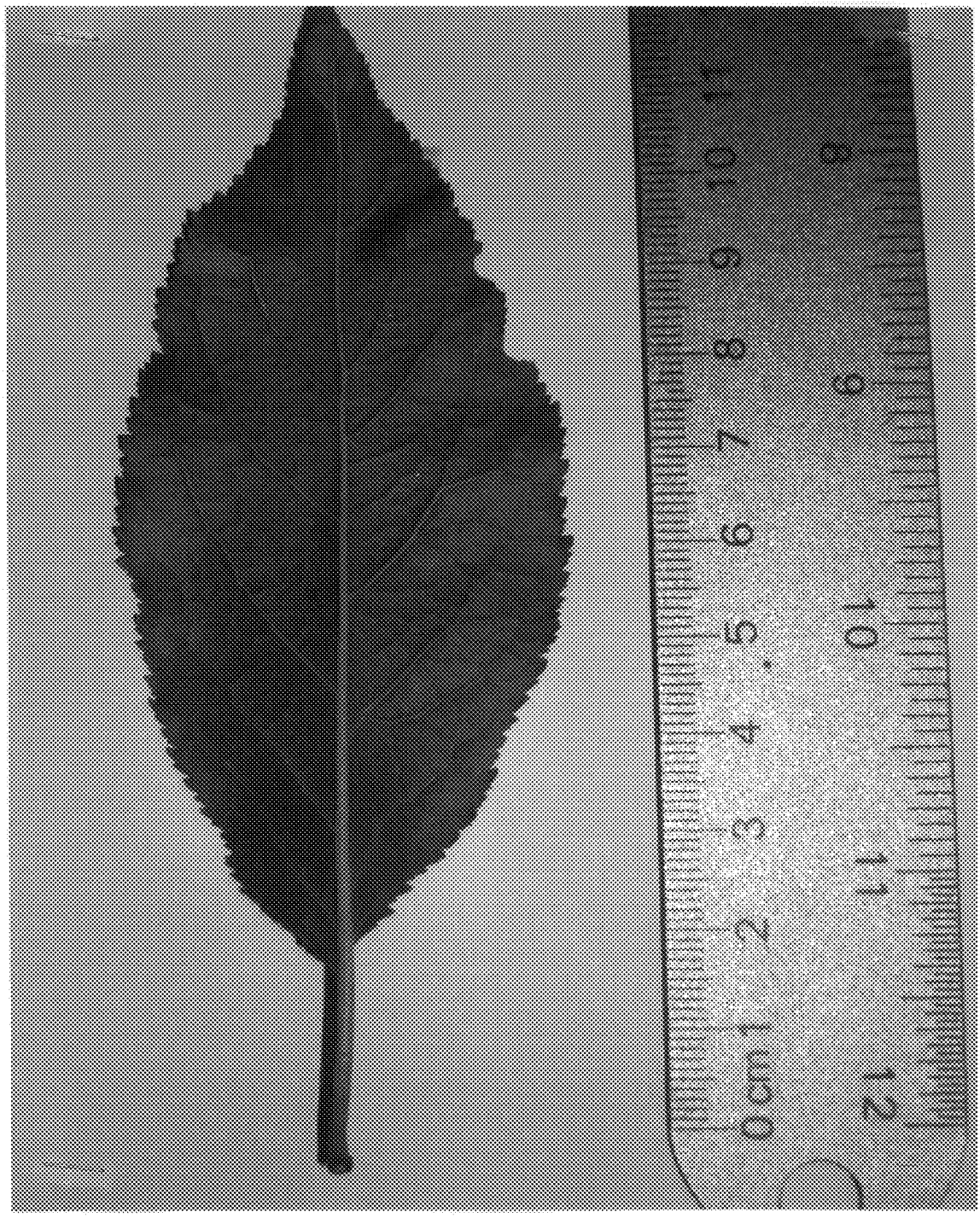

The following detailed description sets forth the characteristics of the new cultivar. The data which defines these characteristics was collected natural field conditions on plants produced by asexual propagation carried out in Reedley, Calif., USA. The plants were grown under normal field conditions with flood irrigation. Color designations are presented with reference to the *A Dictionary of Color* by A. Maerz and M. Rea Paul, Second Edition (1950). Common color names are also occasionally employed.

TREE

Age: 1 year old planting (in 2014).

Height: 1.5-2.2 meters.

Spread: Semi-erect. Width: 1.4 meters. Vigor: Low. Density: Medium. Form: Compact.

Production: Unknown since this is a rootstock; helps produce larger fruit when used with plum varieties.

Growth type: Upright.

Bearing: Non-fruit bearing.

Pathogen resistance: High tolerance to Oak Root Fungus, a fungal disease caused by *Armillaria mellea* that causes *Armellaria* root rot in stone fruit.

Resistance to insects: Unknown.

Resistance to mites: Unknown.

Resistance to viruses: Unknown

Nematode tolerance: Adequate commercial tolerance to root knot nematodes (e.g., *Meloidogyne* 15 spp.) and lesion nematodes (e.g., *Pratylenchus vulnus*).
Rootstock performance: Moderate tree vigor; ideal for high density orchards.
Root sprouts (suckering): Minimal suckering present, and only at crown level.
Anchorage: Good with large, fibrous root system.
Compatibility: Compatible with plum, peach and nectarine varieties.
Vigor: Low (30% less than 'Nemaguard' (*Prunus* 25 *persica*× *P. davidiana*) (unpatented)).

TRUNK

Size: Reduced trunk cross sectional area; from 5-8 cm in diameter.
Surface texture: Fairly smooth with longitudinal scarf.
Bark color: 16-A-5 (Bear Chaetura Drab).
Lenticels:
*Length*.—6-7 mm.
*Width*.—2-3 mm.
*Color*.—7-C-7 (Bonito Fuscous).
*Density*.—Low.
*Orientation*.—Horizontal.

BRANCHES

Diameter: Variable, from 0.5-1 cm. in the same growing season.
Surface texture: Smooth in the current season with incipient longitudinal striae as maturity advances.
Color: 16-L-7 (Bronze Green).
Form: Staggered, alternate. Circular in diameter.
Average angle: Acute.
Bud arrangement: Helicoidal throughout the branch.
Lenticels:
*Length*.—1-2 mm in the first year of growth.
*Width*.—0.5-1 mm.
*Shape*.—Rounded initially in younger tissue; elongated horizontally as branches mature into the season.
*Density*.—Low, but progressing to medium as maturity advances.
*Color*.—15-E-7 (ACORN Meadlowlark+).

LEAVES

Length: 8-13 cm. (at end of season).
Width: 3-4 cm.
Form: Elliptical.
Lower surface texture: Smooth between veins.
Upper surface texture: Smooth/waxy.
Thickness: Medium.
Base: Acute to oblique.
Apex: Acute.
Margin: Crenate around entire leaf.
Pubescence:
*Upper surface*.—Essentially absent; very little pubescence observed only with the aid of a dissecting scope.
*Lower surface*.—Absent.
Color: Young leaves:
*Upper surface*.—23-A-12 (Wintergreen English Ivy+).
*Lower surface*.—31-L-11 (Triton).
Color: Mature leaves:
*Upper surface*.—24-L-8.
*Lower surface*.—23-H-12 (CHROME GR., MDP).
Petiole:
*Shape*.—Straight without a central grove; tapering upwards towards the leaf base. 1 to 3 very small sized plums near the base of the leaf. Petiole devoid of vestigial wings.
*Length*.—1 to 2 cm.
*Diameter*.—1.5 to 3 mm.
*Color*.—19-J-6 (APPLE GREEN).
*Texture*.—Smooth with no pubescence present.
Veins: Venation type, off set dichotomous, raised.
Tree type disposition, overall color:
*Upper surface*.—22-C-12 (Alfalfa).
*Lower surface*.—21-L-12 (Imperial Jade).

FLOWER

The 'A B 207' rootstock of the present invention produces no flowers.

FRUIT

The 'A B 207' rootstock of the present invention produces no flowers and hence no fruit, but helps produce larger fruit with plum varieties such as, without limitation, 'Crimson Glo' (U.S. Plant Pat. No. 12,856) and 'Black Splendor' (unpatented) and Joanna Red' (U.S. Plant Pat. No. 10,385).

GENERAL

Ideal for use as a low vigor rootstock for mainly plum, peach and nectarine varieties, where *Armillaria* root rot is present. May be used as a replant or interplant rootstock.
Winter hardiness: Hardy (under the conditions in Reedley, Calif.).
Bud winter hardiness: High.
Tolerance to root asphyxia: Tolerant.
Drought tolerance: Moderately tolerant.
Disease resistance: Moderate resistance to root-knot nematode (e.g., *Meloidogyne* 15 spp.); resistance to lesion nematodes (e.g. *Pratylenchus vulnus*).
Scionic performance: Induces larger fruit with less need to thin.

SUMMARY

Although the new variety of rootstock possesses the above described characteristics as a result of growing conditions prevailing near Visalia, Calif. in the San Joaquin Central Valley, it is to be understood that variations of the usual magnitude may occur as a result of changes in growing conditions and cultural practices (irrigation, fertilizers, pruning, pest control was well as climate).

Having thus described and illustrated the new variety of rootstock, what is claimed as new and desired to be secured by plant Letters Patent is:

1. A new and distinct variety of rootstock substantially as illustrated and described herein for use primarily with plum, peach or nectarine scions, which is characterized principally by its resistance to *Armillaria* root fungus, its absence of vestigial wings on leaf petioles, and its inducement of larger fruit.

* * * * *